United States Patent [19]

Belecky et al.

[11] Patent Number: 5,672,165
[45] Date of Patent: Sep. 30, 1997

[54] MENSTRUAL HYGIENE PRODUCT

[76] Inventors: June Marian Belecky, 6-113 Elmwood Ave. East, London, Ontario, Canada, N6C 1J5; Sonja Rosa Benetti, 489 St James Street, London, Ontario, Canada, N5W 3P4

[21] Appl. No.: 778,068

[22] Filed: Jan. 6, 1997

Related U.S. Application Data

[63] Continuation of Ser. No. 475,906, Jun. 7, 1995, abandoned, which is a continuation-in-part of Ser. No. 159,604, Dec. 1, 1993, abandoned, which is a continuation of Ser. No. 963,141, Oct. 19, 1992, abandoned.

[51] Int. Cl.⁶ ........................................... A61F 13/15
[52] U.S. Cl. ........................... 604/383; 601/385.1
[58] Field of Search ...................... 604/385.1–402, 604/377–380, 383

[56] References Cited

U.S. PATENT DOCUMENTS

| | | |
|---|---|---|
| Re. 24,137 | 4/1956 | Jacks . |
| 2,331,358 | 10/1943 | Strongson ............... 604/385.1 |
| 3,183,909 | 5/1965 | Roehr . |
| 3,406,089 | 10/1968 | Hicks et al. ............... 604/401 |
| 3,528,422 | 9/1970 | Hodas . |
| 3,726,277 | 4/1973 | Hirschman . |
| 3,905,372 | 9/1975 | Denkinger ............... 604/377 |
| 3,983,873 | 10/1976 | Hirschman . |
| 4,046,147 | 9/1977 | Berg . |
| 4,433,972 | 2/1984 | Malfitano . |
| 4,627,848 | 12/1986 | Lassen et al. . |
| 4,631,062 | 12/1986 | Lassen et al. ............ 604/385.1 |

FOREIGN PATENT DOCUMENTS

| | | |
|---|---|---|
| 2653-328-A | 10/1989 | France . |
| 5-208034 | 8/1993 | Japan ............... 604/385.1 |
| 0242517 | 11/1925 | United Kingdom . |

Primary Examiner—John G. Weiss
Assistant Examiner—K. M. Reichle
Attorney, Agent, or Firm—Jeffrey T. Imai; D. Doak Horne; Arne I. Fors

[57] ABSTRACT

A feminine menstrual hygiene product has an absorbent pad. The pad is in a folded condition. The pad is folded longitudinally and transversely and then folded diagonally presenting an interlabial insert and orthogonally opposed panels. The pad is tacked to retain the absorbent pad in the folded condition. The interlabial insert is positionable fully within the vestibule of a wearer to occlude menstrual fluids. The pad is covered by a hydrophobic web overlying the interlabial insert and opposed panels and an impermeable membrane underlying the opposed panels.

11 Claims, 3 Drawing Sheets

MENSTRUAL HYGIENE PRODUCT

This is a continuation application of application Ser. No. 08/475,906, filed on Jun. 7, 1995 now abandoned, which is a continuation-in-part application of application Ser. No. 08/159,604, filed Dec. 1, 1993, now abandoned, which is a continuation application of application Ser. No. 07/963,141, filed Oct. 19, 1992, now abandoned.

FIELD OF INVENTION

This invention relates to a menstrual hygiene product. In particular, this invention relates to a menstrual hygiene product which has a contoured structure for improved interlabial sealing.

BACKGROUND OF INVENTION

There is a long standing need for an improved feminine hygiene product. There is a broad spectrum of commercially available menstrual hygiene products which include tampons, napkins, various pads, and shields. Even though some of these products are commercially successful, each still has many problems and inadequacies, which to date, have not been fully addressed.

For example, tampons are relatively effective for management of menstrual flow. However, tampons have been associated with "toxic shock syndrome", which could lead to infection, sterility, and even death, if not diagnosed and treated timely.

Moreover tampons are neither convenient nor easy to insert, and their insertion can itself result in minor damage to vaginal tissues. Inserting and maintaining the tampon's position within the vagina is problematic, since adjacent musculature tends to expel the tampon from the body, especially during bowel activity. Removing a tampon is also problematic, with respect to ascertaining in advance when the absorbent material is approaching saturation, and with respect to physically removing the tampon. Once removed, the tampon is not amenable to reinsertion, even in the event that only a small proportion of its overall absorbent capacity remains unused.

The difficulty in ascertaining when a tampon is saturated and needs to be changed is a particular shortcoming for tampons, since the menstrual flows can be highly unpredictable, especially given the surges of menstrual fluid that typically occur without either warning or discernable vaginal sensation. A wearer cannot be confident of how much, or how little time might remain before a change is required. For a greater sense of security, tampons may be changed frequently to reduce the risk of accidental leakage. However, the associated cost of utilizing only a limited portion of a tampon's total absorbent capacity makes the cost of using tampons prohibitively high.

Tampons are effective to the extent that they engage in sealing relation against the surrounding vaginal walls, such that the menstrual flow cannot flow around the tampon. Tampons also have the advantage of being relatively resistant to being dislodged by the wearer's posture.

Napkins of various designs have been employed as an alternative to the problems associated with tampons. However, napkins are problematic in that they have not been able to achieve the high degree of menstrual flow management that can be achieved through the use of tampons.

Napkins rely on the principle of using a pad with a large surface area to provide the necessary absorbency required for absorbing the menstrual flow. Napkins do not establish a sealing relationship against the wearer's body that might otherwise constrain the flow so that it might be absorbed over a small surface area. In this, pads differ fundamentally in their mode of action from tampons.

Since napkins depend in their operation on having a large absorbent surface area, they are typically bulky. In addition, napkins must be held relatively tight against the wearer's body in order to help reduce the chance of menstrual flow bypassing the pad. With regard to relatively recent improvements in absorptive materials, pad designs have been offered in "thin" and "ultra thin" formats, in an attempt to overcome the problems of bulk. At the same time, however, these products by virtue of such "thinness" are intrinsically more difficult to hold in place against the wearer's body, and therefore suffer from a collateral loss of security and overall dependability.

Napkins are subject to bunching up and shifting relative to the wearer's body, particularly with changes in the wearer's posture (i.e. walking, sitting, standing). The napkin is often displaced out of effective juxtaposition with the wearer's body. Such displacement invariably results in leakage as well as discomfort for the wearer.

There are also physiological limitations on just how much absorbent surface area can be provided in the space available adjacent to the wearer's pubis. As a consequence of these intrinsic limitations on the absorbent napkin paradigm, a number of remedial design features have been proposed.

One feature of napkin design which followed from attempts to overcome the intrinsic limitations on the conventional absorbent pad paradigm, is the use of longitudinal channels in the pad material. The objective here is to channel or direct the menstrual flow along the length of the pad. The available surface area in the longitudinal direction is not quite so restricted as it is in the lateral direction. This approach is not as efficacious as might have been hoped. Menstrual flow is subject to gravity, and consequently, the flow tends to move laterally across the pad's surface. This tendency is particularly acute during surges in the menstrual flow rate.

The recognition of the failing of flow directing channels is implicit in the development of what is currently widely advertised as "wings". "Wings" are lateral extensions of the pad that are wrapped around the edges of a wearer's undergarment. They are a necessary adjunct if the napkin is to perform reliably for a wearer since lateral menstrual flow is a fact of life in employing conventional napkin designs.

The fact that the conventional napkin paradigm is driven on the basis of providing as much absorbent surface area as possible, has led to proposals for vulva insert extensions on the pads. This represents an attempt to increase the absorbent surface area within the intrinsic physiological limitations. Nevertheless, these approaches to date have not been successful in departing from the conventional napkin paradigm. Moreover, the designs to date have not been able to sufficiently increase the surface area to reliably manage menstrual "overflow" and leakage remains a chronic problem with even these augmented pad designs.

Exemplary amongst these products, are those proposed by Berg and Pigneul in their respective patents, U.S. Pat. No. 4,046,147 and French Patent No. 2,653,328. Both patents relate to pads that are augmented through the use of a vulva insert and relate to designs that are intended to channel flow longitudinally along the length of the napkin.

Accordingly, the prior attempts at increasing the available surface area in conventional pad designs and even prior attempts at augmenting surface area through the use of vulva inserts, have not successfully addressed the long standing need for a reliable, comfortable product that can manage menstrual flow. To date, only the tampon "sealing" paradigm has been reliable for managing menstrual flow, but this approach continues to be faced with the problems of vaginal insertion and the other complications mentioned above.

SUMMARY OF THE INVENTION

The disadvantages of the prior art may be overcome by providing a feminine menstrual hygiene product which has an absorbent pad in a folded condition. The pad is folded longitudinally and transversely and then folded diagonally presenting an interlabial insert and orthogonally opposed panels.

In one aspect of the invention, the absorbent pad is in a thrice folded condition. The pad is folded once longitudinally and once transversely and then folded diagonally presenting an interlabial insert and orthogonally opposed panels. The interlabial insert is positionable fully within the vestibule of a wearer to occlude menstrual fluids.

According to one aspect of the invention, there is provided a feminine menstrual hygiene product having an absorbent pad of layers of absorbent sheets. The pad has a longitudinal and transverse extent having a ratio in the range of 4:1 to 5:1. The pad is in a thrice folded condition, with the pad folded in half longitudinally and transversely and then folded diagonally presenting an interlabial insert and panels extending orthogonally therefrom. The interlabial insert is positionable fully within the vestibule of a wearer to occlude menstrual fluids. A stitch is made along the diagonal fold to retain the absorbent pad in the folded condition. A covering encases the absorbent pad.

DESCRIPTION OF THE DRAWINGS

The invention will be better understood with reference to the following figures and description.

Like references refer to like parts on the figures.

DETAILED DESCRIPTION OF THE INVENTION

Figure 1:
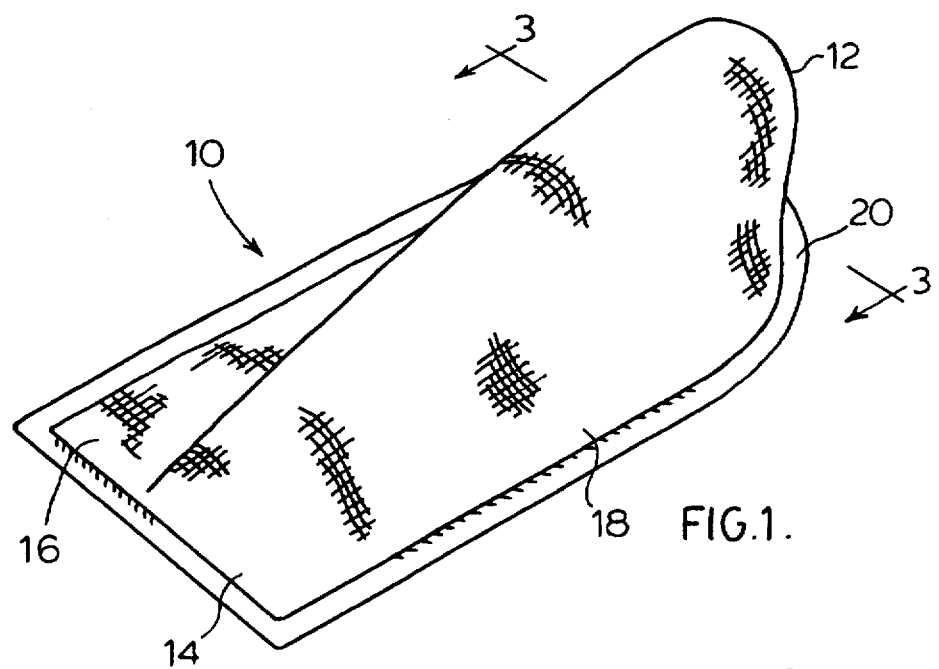
FIG. 1 is an illustration of a top perspective view of an embodiment of the menstrual hygiene product of the invention in the folded condition.
Figure 2:
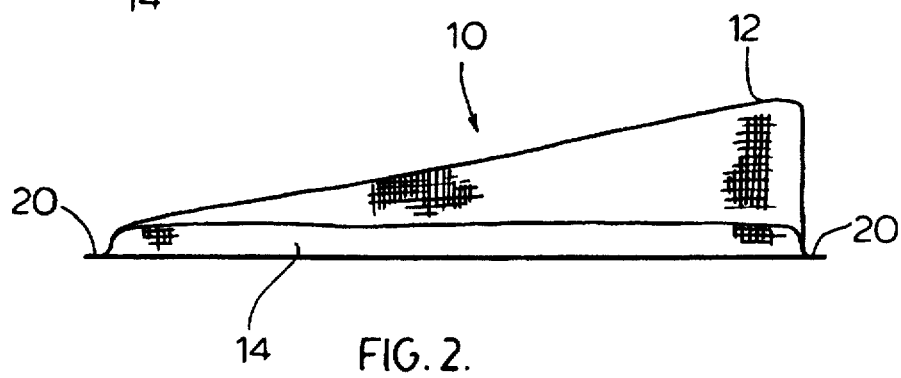
FIG. 2 is an illustration of a side view of the menstrual hygiene product of FIG. 1.

The feminine menstrual hygiene product 10 of the present invention is illustrated in FIGS. 1 and 2.

The hygiene product 10 of the present invention has an interlabial insert 12 and opposed panels 14 and 16. The hygiene product 10 is encased in a cover 18, which is sealed along the outer edge 20 of panels 14 and 16.

Figure 3:
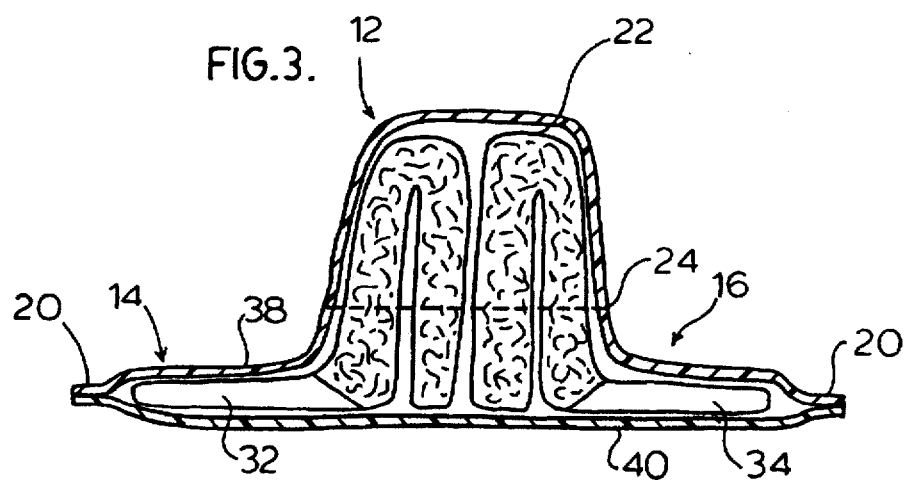
FIG. 3 is an illustration of a cross sectional view taken along line 3—3 of the menstrual hygiene product of FIG. 1.
Figure 4:
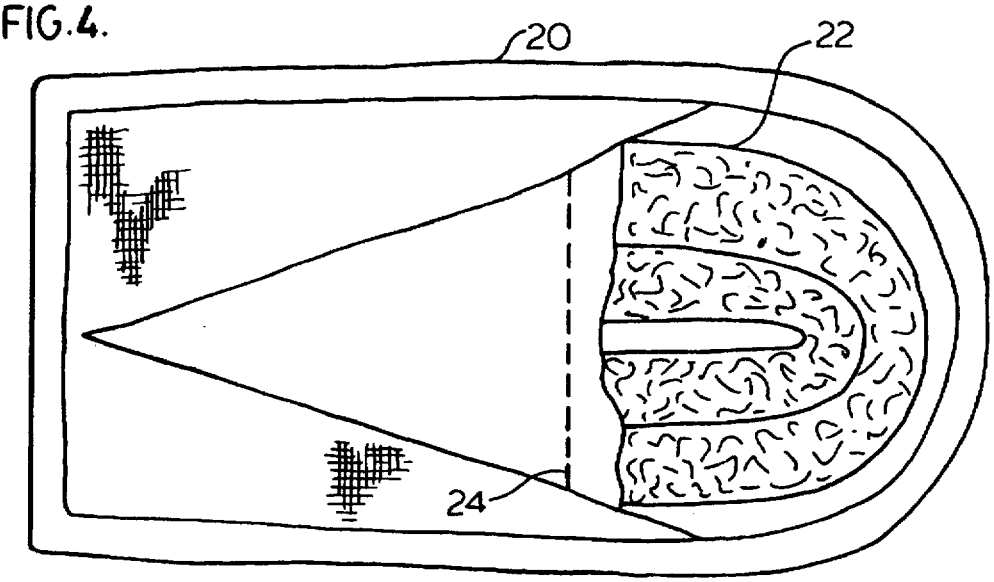
FIG. 4 is an illustration of a top view with a cut away portion of the menstrual hygiene product of FIG. 1.

Referring to FIGS. 3 and 4, the general construction and shape of the hygiene product 10 is illustrated. In plan view, the hygiene product has a generally bullet-shape outline. It is readily understood that the outline can be contoured to any desired shape.

The hygiene product 10 has an absorbent pad 22, which is preferably thrice folded. The folds of the absorbent pad 22 are retained in its general position by stitch 24. Stitch 24 is a thread which is threaded through absorbent pad 22 for retaining the folded portions together.

Figure 5:
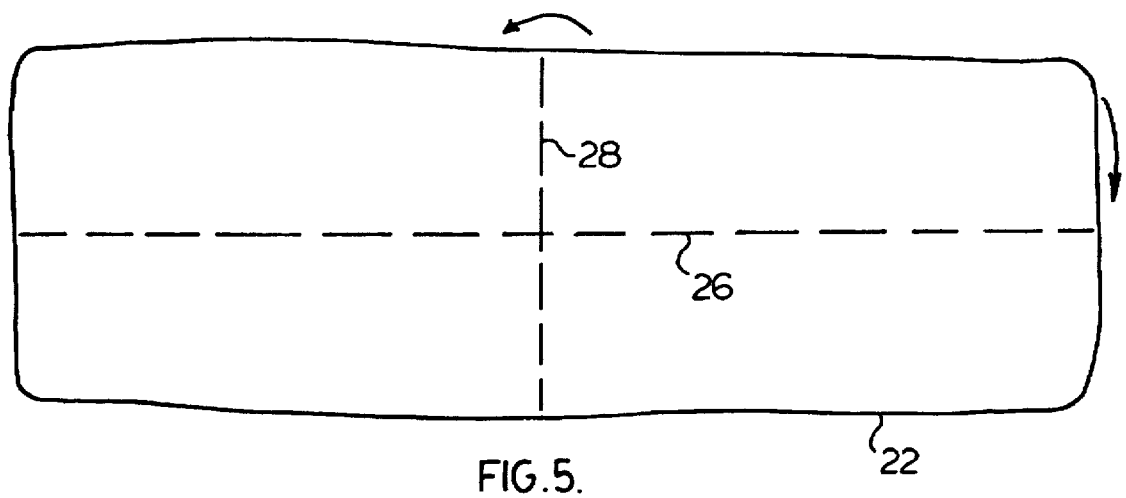
FIG. 5 is an illustration of a top view of an embodiment of the absorbent pad used to make the menstrual hygiene product of FIG. 1 in the unfolded condition with a schematic illustration of how the absorbent pad is folded longitudinally and transversely.
Figure 6:
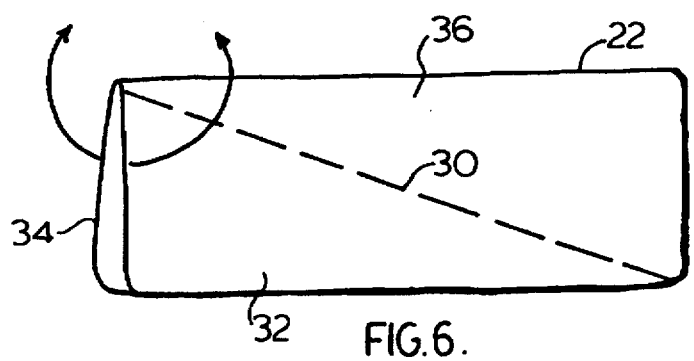
FIG. 6 is a schematic illustration of a side view of the absorbent pad of FIG. 5 after the absorbent pad has been folded longitudinally and transversely with a broken line indicating where to fold the absorbent pad diagonally.

Referring to FIGS. 5 and 6, the folding of the absorbent pad is illustrated. Absorbent pad 22 can be made from a single batt of absorbent fibres, which are commonly used in the manufacture of feminine hygiene products. Alternatively, layers of sheets of absorbent fibres, such as those used in ultra thin absorbent feminine hygiene pads may also be used in the present invention.

The thickness of the absorbent pad 22 in the unfolded condition is generally that of a conventional napkin. The conventional napkin may be an ultra thin, thin, regular, mini or maxi napkin depending on the absorbency required for absorbing the menstrual flow.

Absorbent pad 22 has a generally elongate shape, having a longitudinal extent 26 and a transverse extent 28.

Typically, the longitudinal extent 26 of the absorbent pad 22 to the transverse extent 28 will have a ratio of between 4:1 to 5:1. Other ratios may be used to specifically configure the finished product. In other words, higher or lower ratios may be used to manufacture larger and smaller hygiene products of the present invention.

The absorbent pad 22 is first folded along its longitudinal extent 26 and then along the transverse extent 28 to produce a twice folded absorbent pad as schematically illustrated in FIG. 6.

Although the preferred method of folding absorbent pad 22 is first along the longitudinal extent 26 and then along the transverse extent 28, similar results may be obtained by folding first along the transverse extent 28 and then along the longitudinal extent 26. Furthermore, the absorbent pad 22 can be folded several times in the longitudinal direction.

Referring to FIG. 6, the twice folded absorbent pad 22 is then folded along the diagonal extent 30. Opposed flaps 32 and 34 are folded in opposite directions until they extend substantially orthogonal to the folded section 36 of absorbent pad 22. The folded section 36 forms the interlabial insert 12, while the flaps 32 and 34 form the panels 14 and 16.

Referring back to FIG. 3 and 4, the folds of the absorbent pad 22 are now more clearly understood. By thrice folding the absorbent pad 22 for forming the interlabial insert 12, the absorbent pad 22 had additional integrity to be fully inserted into the vestibule of the wearer.

Although the FIGS. 3 and 4 illustrate the absorbent pad 22 as being loosely tacked together by stitch 24, the preferred embodiment stitch 24 is tightly bound in order to give the interlabial insert 12 a more bulbous shaping. Alternatively, other tacking methods known in the art may also be used. Further, with the use of certain absorbent materials which make up absorbent pad 22, pressing and compressing the folded absorbent pad may be sufficient to retain the absorbent pad 22 in the desired shape, making stitch 24 unnecessary. Further, starch or other suitable additives may be used to maintain the absorbent pad 22 in a folded condition.

The cover 18 comprises an overlying web 38 of a generally hydrophobic material. The hydrophobic material allows fluid to pass therethrough and be absorbed by the absorbent pad 22. The hydrophobic material of web 38 gives the product a "stay-dry" character. The underside of cover 18 is an impermeable layer 40. Web 38 and layer 40 are joined together at the outer edge 20 by any suitable means. Heat sealing or thermosealing is a method which is widely used in the art. As shown in the embodiments of FIGS. 3 and 7, stitch 24 can be used to tack said cover 18 in close proximity to said absorbent pad.

Figure 7:
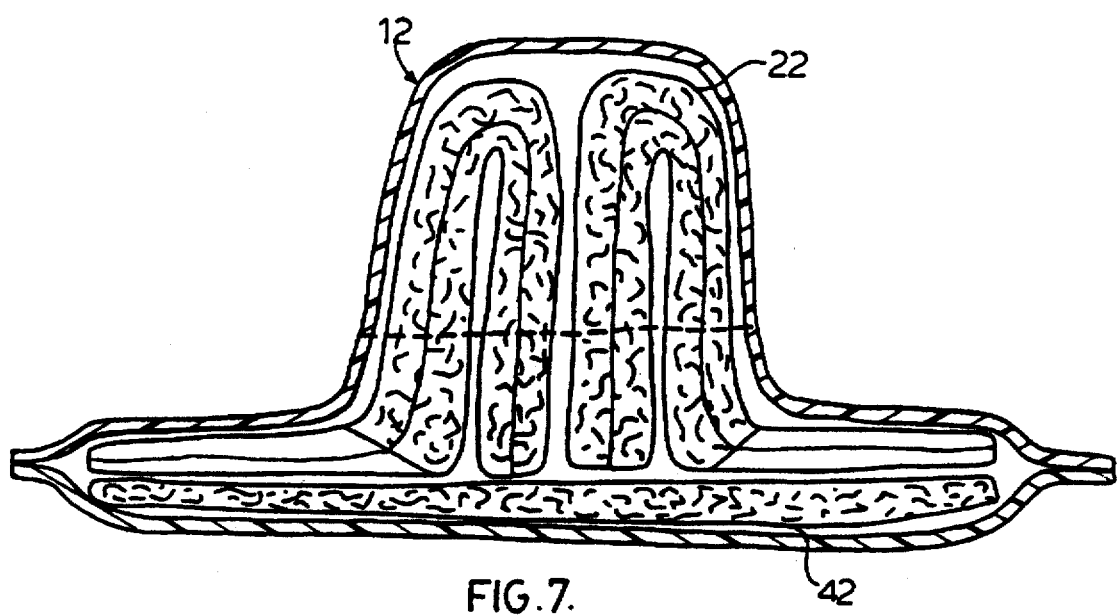
FIG. 7 is an illustration of a cross-sectional view of the menstrual hygiene product of FIG. 1 with an additional absorbent pad.

Referring now to FIG. 7, a second embodiment of the present invention is illustrated. The second embodiment is identical to the first embodiment, except that an additional absorbent pad 42 underlies and is affixed to the absorbent pad 22. The additional absorbent pad 42 increases the absorbency capacity of the hygiene product and places absorbent material where the thrice folded absorbent pad 22 is unable to cover.

In use, both embodiments are used in the same manner. The interlabial insert is placed in the vestibule of the wearer. The larger end of interlabial insert 12 is the posterior end of the hygiene product, whereas the opposite end is the anterior end. The anterior end will overlay the labia majora. The posterior end is positionable adjacent and along the posterior end wall of the vestibule. In this position, the majority of the absorbent pad 22 is positioned strategically in the menstrual flow. As a result, the hygiene product 10 will fully occlude the menstrual flow.

The interlabial insert 12 has an advantageous shape. The shape presented by the folding of the absorbent pad 22 in the manner described above allows the interlabial insert 12 to be fully inserted into the vestibule of the wearer. In doing so, the labia majora of the wearer will conform to the shape of the interlabial insert 12 and will grasp the hygiene product 10 to hold it in place. This grasping will seal the hygiene product 10 to the wearer to fully occlude the menstrual flow.

It is now apparent to a person skilled in the art that there are numerous other modifications of this invention. It is understood that certain changes in design, size, and components may be effective, without a departure from the spirit of the invention, and within the scope of the appended claims.

We claim:

1. A feminine menstrual hygiene product comprising an absorbent pad having opposite sides, opposite ends, corners defined at intersections of the sides and ends, respectively, and a longitudinal extent greater than a transverse extent, said absorbent pad comprising layers of absorbent sheets in a thrice folded condition, said pad folded once longitudinally end to end, then folded once transversely side to side, and then folded once diagonally corner to corner, the portion of the pad on one side of the diagonal fold adjacent the longitudinal fold and transverse fold presenting a folded insert having a structural integrity from said folds for positioning within a labia and the portion of the pad on the other side of the diagonal fold presenting opposed panels extending orthogonally from said insert, said insert being fully positionable within a vestibule of a wearer to occlude menstrual fluids, and a covering encasing said absorbent pad.

2. A feminine menstrual hygiene product as claimed in claim 1 wherein said product further comprises a retaining means for retaining said absorbent pad in the folded condition.

3. A feminine menstrual hygiene product as claimed in claim 2 wherein said retaining means is a stitch along said diagonal fold.

4. A feminine menstrual hygiene product as claimed in claim 1 wherein said absorbent pad has a contoured outer perimeter whereby upon being folded said panels have a bullet-shaped outline.

5. A feminine menstrual hygiene product as claimed in claim 1 wherein said longitudinal extent to said transverse extent has a ratio in the range of 4:1 to 5:1.

6. A feminine menstrual hygiene product as claimed in claim 1 wherein said covering comprises a hydrophobic web overlying said insert and said panels and an impermeable membrane for underlying said panels.

7. A feminine menstrual hygiene product as claimed in claim 1 wherein said covering comprises a hydrophobic web overlying said insert and said panels, said hydrophobic web sealed to an impermeable membrane underlying said panels.

8. A feminine menstrual hygiene product as claimed in claim 1 wherein said absorbent pad further comprises an unfolded absorbent mat.

9. A feminine menstrual hygiene product as claimed in claim 8 wherein said panels are affixed to said unfolded absorbent mat.

10. A feminine menstrual hygiene product comprising an absorbent pad of layers of absorbent sheets, said pad having opposite sides, opposite ends, corners defined by intersections of the sides and ends, respectively, and a longitudinal extent and a transverse extent having a ratio in the range of 4:1 to 5:1, said pad being in a thrice folded condition, said pad folded once in half longitudinally end to end and once in half transversely side to side and then folded once diagonally corner to corner, the portion of the pad on one side of the diagonal fold adjacent the longitudinal fold and the transverse fold presenting a folded insert having a structural integrity from said folds adapted for positioning within a labia and the portion of the pad on the other side of the diagonal fold presenting opposed panels extending orthogonally therefrom, said insert positionable fully within a vestibule of a wearer to occlude menstrual fluids, a stitch along a diagonal fold for retaining said absorbent pad in the folded condition, and a covering encasing said absorbent pad.

11. A feminine menstrual hygiene product as claimed in claim 10 wherein said covering comprises a hydrophobic web overlying said insert and said panels, said hydrophobic web sealed to an impermeable membrane underlying said panels.

* * * * *